United States Patent
Jordan et al.

(10) Patent No.: US 9,758,464 B2
(45) Date of Patent: Sep. 12, 2017

(54) CONTINUOUS FLOW PROCESS FOR THE PREPARATION OF INGENOL-3-MEBUTATE

(71) Applicant: Alphora Research Inc., Mississauga (CA)

(72) Inventors: Robert W. Jordan, Rockwood (CA); Craig Dixon, Brooklin (CA); Boris Gorin, Oakville (CA)

(73) Assignee: Alphora Research Inc. (CA)

( * ) Notice: Subject to any disclaimer, the term of this patent is extended or adjusted under 35 U.S.C. 154(b) by 0 days.

(21) Appl. No.: 15/313,226

(22) PCT Filed: Apr. 10, 2015

(86) PCT No.: PCT/CA2015/050300
§ 371 (c)(1),
(2) Date: Nov. 22, 2016

(87) PCT Pub. No.: WO2015/176175
PCT Pub. Date: Nov. 26, 2015

(65) Prior Publication Data
US 2017/0190652 A1    Jul. 6, 2017

Related U.S. Application Data

(60) Provisional application No. 62/002,445, filed on May 23, 2014.

(51) Int. Cl.
*C07C 67/08*    (2006.01)
(52) U.S. Cl.
CPC .......... *C07C 67/08* (2013.01); *C07C 2103/98* (2013.01)
(58) Field of Classification Search
CPC .................................................... C07C 67/08
See application file for complete search history.

(56) References Cited

U.S. PATENT DOCUMENTS

| 7,449,492 B2 | 11/2008 | Aylward et al. | |
| 2013/0177952 A1* | 7/2013 | Hogberg | C07C 67/297 435/135 |

FOREIGN PATENT DOCUMENTS

| WO | 2012010172 A1 | 1/2012 |
| WO | 2013110753 A1 | 8/2013 |
| WO | WO 2013/110753 A1 * | 8/2013 |
| WO | 2014012836 A1 | 1/2014 |

OTHER PUBLICATIONS

Sayed, M.D. et.al. ; Experienta, (1980), 36, 1206-1207.
Hohmann, J. et. al; Planta Med., (2000), 66, 291-294.
Du et al., "Lipase-Catalyzed Regioselective Acylation of Sugar in Microreactors", RSC Adv. 2012, 2,2663-2665.
Migliorini et al., "Regioselective Enzymatic Diol Esterification in Batch and Fixed-Bed Adsorptive Reactors: Experiments and Modeling", Biotechnol. Prog. 2000, 16, 600-609.
International Search Report and Written Opinion for PCT/CA2015/050300, date of mailing Nov. 26, 2015, 12 pages.

* cited by examiner

*Primary Examiner* — Paul A Zucker
(74) *Attorney, Agent, or Firm* — Luedeka Neely Group, P.C.

(57) ABSTRACT

Disclosed is a continuous process for the preparation of ingenol-3-mebutate by reaction, in solution, of ingenol or ingenol anion and angelic anhydride or an equivalent angelylating agent. The continuous flow process is preferably performed in the presence of a base such as lithium hexamethyl disilazane (LiHMDS) and/or an activating agent such as dicyclohexylcarbodiimide (DCC). Also disclosed is a process for recycling the other reaction products obtained in the continuous process for preparation of ingenol-3-mebutate for formation of ingenol, which can then be recycled to form ingenol-3-mebutate.

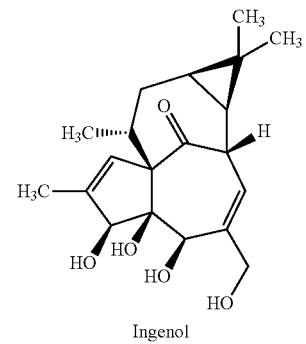

Ingenol

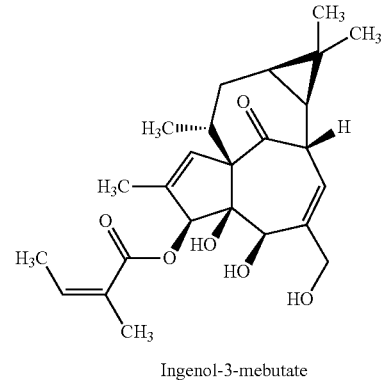

Ingenol-3-mebutate

22 Claims, No Drawings

CONTINUOUS FLOW PROCESS FOR THE PREPARATION OF INGENOL-3-MEBUTATE

This application is a Section 371 national phase entry of PCT application PCT/CA2015/050300, filed Apr. 10, 2015. This application also claims the benefit of the earlier filing date of U.S. provisional patent application 62/002,445, filed Apr. 23, 2014.

CROSS REFERENCE TO RELATED APPLICATION

This application claims the benefit of and priority to U.S. Provisional Patent Application Ser. No. 62/002,445 filed May 23, 2014 under the title A NOVEL CONTINUOUS FLOW PROCESS FOR THE PREPARATION OF INGENOL-3-ANGELATE. The content of the above patent application is hereby expressly incorporated by reference into the detailed description hereof.

FIELD

The specification relates to a continuous flow process for preparation of ingenol-3-mebutate from ingenol.

BACKGROUND

Ingenol-3-mebutate (trade-name: Picato®) has been disclosed as protein kinase C activator that can be used for the treatment of actinic keratosis (WO 2012/010172, incorporated herein by reference). Ingenol-3-angelate (Sayed, M. D. et.al.; Experienta, (1980), 36, 1206-1207, incorporated herein by reference) can be isolated from various *Euphorbia* species, and particularly from *Euphorbia peplus* (Hohmann, J. et. al; Planta Med., (2000), 66, 291-294, incorporated herein by reference) and *Euphorbia drummondii* by extraction followed by chromatography as described in U.S. Pat. No. 7,449,492, incorporated herein by reference.

Ingenol-3-mebutate is also known as ingenol-3-angelate, 2-methyl-2(Z)-butenoic acid (1aR,2S,5R,5aS,6S,8aS,9R,10aR)-5,5a-dihydroxy-4-(hydroxymethyl)-1,1,7,9-tetramethyl-11-oxo-1a,2,5,5a,6,9,10,10a-octahydro-1H-2,8a-methanocyclopenta[a]cyclopropa[e]cyclodecen-6-yl ester; PEP005, ingenol mebutate, with an IUPAC name: (1aR,2S,5R,5aS,6S,8aS,9R,10aR)-5,5a-Dihydroxy-4-(hydroxymethyl)-1,1,7,9-tetramethyl-11-oxo-1a,2,5,5a,6,9,10,10a-octahydro-1H-2,8a-methanocyclopenta[a]cyclpropa[e][10]annulen-6-yl(2Z)-2-methylbut-2-enoate. The chemical formula for ingenol-3-mebutate is $C_{25}H_{34}O_6$ having a molecular weight of 430.53 g/mol. The chemical structure of ingenol-3-mebutate is shown below, along with numbering of some atoms that are referred to herein.

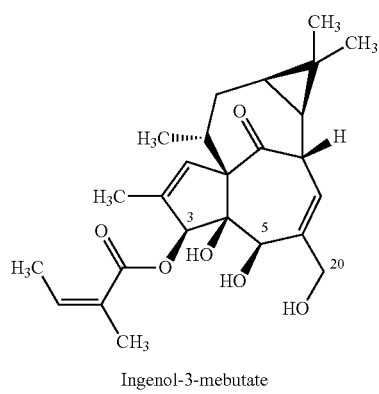 [SMILES: C/C=C(/C)C(=O)O[C@H]1C(C)=C[C@]23C(=O)[C@@H](C=C(CO)[C@@H](O)[C@]12O)[C@H]1[C@@H](C[C@H]3C)C1(C)C]

Ingenol-3-mebutate

WO 2012/010172 (incorporated herein by reference) discloses a process for preparation of ingenol-3-mebutate from ingenol (structure shown below) involving reacting one or both hydroxyl groups in positions 5 and 20 of ingenol with a suitable hydroxyl protecting agent, and where the hydroxyl protecting group are the same or different, to obtain an intermediate compound (hydroxyl protected ingenol). An esterification reaction is then carried out on the intermediate compound to esterify the hydroxyl group at the 3-position to form a hydroxyl protected ingenol-3-mebutate. Subsequently, the hydroxyl protecting groups are removed to obtain ingenol-3-mebutate.

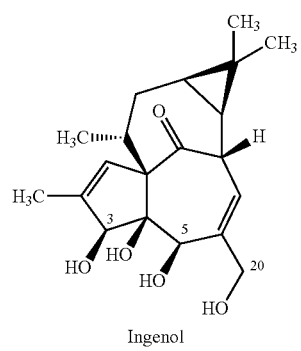

Ingenol

WO 2014/012836 (incorporated herein by reference) discloses an alternate process for preparation of ingenol-3-mebutate from 20-deoxy-ingenol by selective angeloylation to 20-deoxy-ingenol-3-angelate, followed by oxidation to ingenol-3-angelate.

The processes disclosed in WO 2012/010172 and WO 2014/012836 are batch processes, which can require intermittent introduction of frequently changing raw materials, varying process conditions within the vessel, and different purification methods. Typically, in batch processing, vessels are often idle while waiting for raw materials or undergoing quality control checks and cleaning. In contrast, a continuous operation can allow a constant feed of raw materials to the process vessel and continual product withdrawal. Moreover, a continuous process can provide a number of benefits, while also generally being more economical than batch processes.

There is a need in the art for an alternate process for preparation of ingenol-3-mebutate. In addition, there is a need in the art for a process for regioselective preparation of ingenol-3-mebutate from ingenol. Further, there is a need in the art for a continuous process for preparation ingenol-3-mebutate.

SUMMARY OF INVENTION

In one aspect, the specification discloses a continuous process for preparation of ingenol-3-angelate, the process containing the steps of:
  charging using a first line, in a continuous flow, a solution containing ingenol or ingenol anion to a first reaction mixing vessel or mixing line;
  charging using a second line, in a continuous flow, a solution containing angelic anhydride or an equivalent angelylating agent to a first reaction mixing vessel or mixing line;
  permitting reaction of ingenol or ingenol anion with angelic anhydride or the equivalent angelylating agent in the first reaction mixing vessel or mixing line to form a reaction mixture containing ingenol-3-mebutate; and discharging, in a continuous flow, the reaction mixture from the first reaction mixing vessel or mixing line for quenching the reaction mixture.

DESCRIPTION OF EXAMPLE EMBODIMENTS

As disclosed above, in one aspect the specification discloses a continuous process for preparation of ingenol-3-angelate, the process containing the steps of:

charging using a first line, in a continuous flow, a solution containing ingenol or ingenol anion to a first reaction mixing vessel or mixing line;

charging using a second line, in a continuous flow, a solution containing angelic anhydride or an equivalent angelylating agent to a first reaction mixing vessel or mixing line;

permitting reaction of ingenol or ingenol anion with angelic anhydride or the equivalent angelylating agent in the first reaction mixing vessel or mixing line to form a reaction mixture containing ingenol-3-mebutate; and discharging, in a continuous flow, the reaction mixture from the first reaction mixing vessel or mixing line for quenching the reaction mixture.

A continuous process as used herein is not particularly limited, and should be known to a person of ordinary skill in the art. In general, for example and without limitation, a continuous process can allow a continuous flow of reactants that can be charged in a reactor, vessel or line, allowing mixing or reaction of the reactants to form products. This is followed by continuous flow (discharge) of the products from the reactor, vessel or line. Thus, a continuous process can be considered as a process where reactants are charged or fed into a reactor, vessel or line, while a product is simultaneously removed during part of the reaction process. A continuous flow process can allow a single step or multiple steps to be performed, where each step independently of the other can be a reaction, separation or purification.

The terms reactor or vessel as used herein are not particularly limited and should be known to a person of skill in the art. In general, a reactor or vessel relates to, for example and without limitation, a container or vat designed to receive chemicals for a chemical process, such as a chemical reaction. In a continuous process, the reactor or vessel can be designed to receive continuous charge of the reactants, optionally, a residence time of the reactants within the reactor or vessel, to allow mixing and/or reaction of the reactants to form the products, followed by a continuous discharge of the products. The reactor or vessel can be provided with means, such as, an agitator or baffles to allow mixing of the reactants.

The term line as used herein is not particularly limited and should be known to a person of skill in the art. In general, a line refers to, for example and without limitation, a tube, conduit or pipe for conveying or transporting fluids. In a continuous process, the line can be designed to allow charging and/or discharging of fluids, such as reactants or products. In addition, the line (such as, in a reaction mixing line) can be designed to receive reactants and allow mixing and/or reaction of the reactants. Where the line is designed to receive reactants, the size and shape of the line can be adapted to enhance mixing and permit flow of the reactants into the line, minimizing back pressure.

The term solution as used herein is not particularly limited and should be known to a person of skill in the art. In general, a solution is a homogeneous mixture composed of only one phase. In such a mixture, a solute is a substance dissolved in another substance, known as a solvent. The solvent does the dissolving. The solution more or less takes on the characteristics of the solvent including its phase and the solvent is commonly the major fraction of the mixture. The term solution as used herein can include a mixture having some solids that are not present in solution or insoluble in the solvent, so long as they do not interfere with the overall reaction and process.

The solvent used for the process disclosed herein is not particularly limited and can be determined. In one embodiment, for example and without limitation, the solvent is selected to allow reaction of the reactants to occur without interfering with the solvent, and preferably, promoting formation of ingenol-3-mebutate. The solvent is preferably an aprotic solvent, that is, a solvent that cannot donate hydrogen. In a further embodiment, for example and without limitation, the solvent is toluene, tetrahydrofuran, methyl-tert-butylether (MTBE), or 2-methyltetrahydrofuran. In a particular embodiment, for example and without limitation, the solvent is 2-methyltetrahydrofuran.

The term equivalent angelylating agent as used herein is not particularly limited and should be known to a person of skill in the art. Equivalent angelylating agents of angelic anhydride include compounds that can be used for reaction with ingenol to form ingenol-3-mebutate. Some equivalent angelylating agent can require activation, a basic condition or both. For example and without limitation, equivalent angelylating agent of angelic anhydride can include angelic acid, angelic acid mixed anhydrides, angelic esters, or angelic acid halides.

The term quenching as used herein is not particularly limited and should be known to a person of skill in the art. In general, and for example and without limitation, quenching a reaction involves manipulations to deactivate any unreacted reagents, cooling the reaction mixture or adding an antisolvent to induce precipitation, collecting or removing the solids by filtration, decantation, or centrifugation, removal of solvents by evaporation, separating the reaction mixture into organic and aqueous layers by liquid-liquid extraction or purification by chromatography, distillation or recrystallization.

In a preferred aspect, the specification relates to synthesis of ingenol-3-mebutate via a continuous process commencing from ingenol as depicted in Scheme 1. In carrying out the process, in one embodiment, ingenol can initially be made to react with a base to deprotonate a hydroxyl group on ingenol and provide an anionic form of ingenol. The anionic form of ingenol can then be made to react with angelic anhydride to form a mixture of regioisomers, including: ingenol-3-mebutate, ingenol-5-mebutate, ingenol-20-mebutate and ingenol-3,20-mebutate. Finally, the reaction mixture is quenched using, for example and without limitation, an acidic solution. Ingenol-3-mebutate can be isolated from the mixture of regioisomers using chromatography and/or crystallization. Moreover, the process also offers the opportunity to recycle the separated, undesired regioisomers (mainly ingenol-5-mebutate, ingenol-20-mebutate and ingenol-3,20-mebutate) to ingenol via hydrolysis, preferably base catalyzed hydrolysis. This can allow for increasing the throughput and overall yield of ingenol-3-mebutate.

Scheme 1: Continuous process for preparation of ingenol-3-mebutate from ingenol.

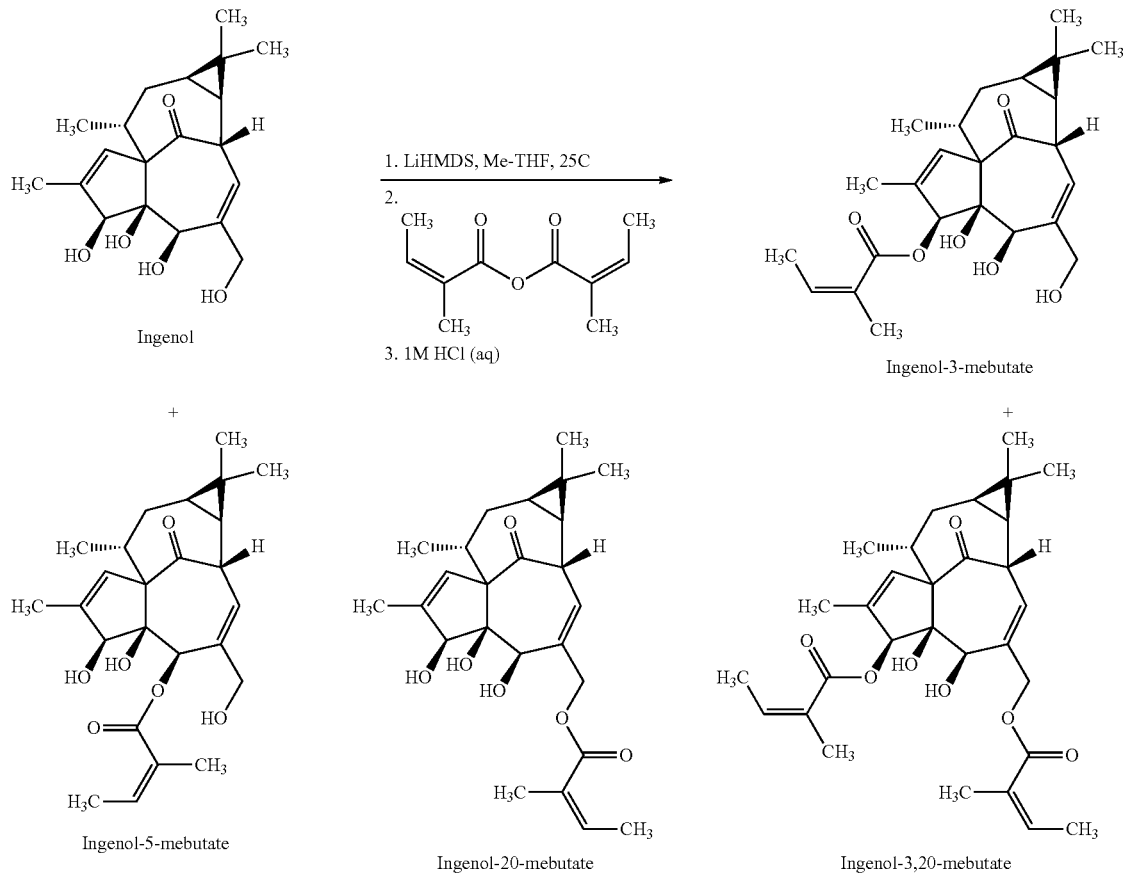

The term 'base' as used herein is not particularly limited and should be known to a skilled worker or can be determined. As used herein, a base is a species that can accept a proton, or a species that donates a pair of electrons. In a preferred embodiment, the base as used in the process disclosed herein can allow deprotonation of the hydroxyl protecting groups to form an ingenol anion. In addition, the base and the conditions for its use, such as concentration, flow-rates, temperature, and others are such that they preferably deprotonate the hydroxyl proton, and avoid and/or minimize deprotonation at other sites, such as the proton alpha to the ketone group. In an alternate embodiment, the base used can donate a pair of electrons to accept protons that result from formation of an acid. Bases can include, for example and without limitation, sodium hydride, lithium hydride, butyl lithium (Bu-Li), tert-butyl lithium (t-BuLi), butyl potassium (BuK), lithium hexamethyl disilazane (LiHMDS) ($C_6H_{18}LiNSi_2$), 2,2,6,6-tetramethylpiperidine, sodium bis(trimethylsilyl)amide ($C_6H_{18}NNaSi_2$), sodium amide ($NaNH_2$), potassium bis(trimethylsilyl)amide ($C_6H_{18}KNSi_2$), triethylamine, pyridine, imidazole, piperidine, 2,6-lutidine, lithium dimethylamide ($C_2H_6LiN$), Lithium diisopropylamide ($C_6H_{14}LiN$), Lithium diethylamide ($C_4H_{10}LiN$), Lithium dicyclohexylamide ($C_{12}H_{22}LiN$), diisopropylethylamine (DIPEA), ethylamine, 4-(dimethylamino)pyridine, or 1,4-diazabicyclo[2.2.2]octane (Dabco®). In a particular embodiment, for example and without limitation, the base is a strong base, such as, sodium hydride, lithium hydride, butyl lithium (Bu-Li), tert-butyl lithium (t-BuLi), butyl potassium (BuK), lithium hexamethyl disilazane (LiHMDS) ($C_6H_{18}LiNSi_2$), sodium bis(trimethylsilyl)amide ($C_6H_{18}NNaSi_2$), or potassium bis(trimethylsilyl)amide ($C_6H_{18}KNSi_2$).

In addition to the above, the concentration and flow-rate of the base are not particularly limited and can be determined. Particularly, as noted-above, concentrations and flow-rates that lead to a 1:1 reaction between ingenol and angelic anhydride or equivalent angelylating agent are preferred. Moreover, as noted above, concentrations or flow-rates that can lead to deprotonation at the α-position to the ketone are not particularly desirable.

The process of the invention preferably makes use of an ingenol anion, which can be obtained by reacting ingenol with a base to deprotonate a hydroxyl group. The process for reacting ingenol with a base is not particularly limited, and can be carried out as a batch reaction or as continuous process. If the process is carried out as a batch reaction, ingenol can be made to react with the base in a preparatory vessel, where ingenol or the anionic form of ingenol can be held or stored till use with reaction with angelic anhydride or an equivalent angelylating agent. The method for carrying out the batch reaction is not particularly limited and can be determined by a person of ordinary skill in the art. For example and without limitation, ingenol in solution can be charged to the preparatory vessel at room temperature, followed by charging of the base (optionally in solution) at room temperature and agitating the solution for a sufficient time period to allow formation of the anionic form of ingenol.

Alternatively, the process for reacting ingenol with the base is carried in a continuous process. Such a continuous process is noted herein as a preliminary continuous process, as it is carried out prior to the continuous process for reaction of the anionic ingenol with angelic anhydride or equivalent angelylating agent. In one embodiment, the preliminary continuous process can be carried out separately from the continuous process for reacting anionic ingenol with angelic anhydride or an equivalent angelylating agent. In another embodiment, the preliminary continuous process can be coupled to and in fluid communication with the continuous process for reacting anionic ingenol with angelic anhydride or an equivalent angelylating agent, such that the anionic form of ingenol is charged, in a continuous flow, to the subsequent continuous process for reacting anionic ingenol with angelic anhydride or an equivalent angelylating agent.

In one embodiment, the preliminary continuous process contains the steps of:

charging, in a continuous flow, ingenol to a preparatory reaction vessel or line;

separately charging, in a continuous flow, the base to the preparatory reaction vessel or line;

permitting the ingenol to mix and/or react with the base to form the solution containing ingenol or ingenol anion; and discharging, in a continuous flow, the solution containing ingenol or ingenol anion from the preparatory reaction vessel or line.

The terms preparatory reaction vessel or line as used herein are not particularly limited and should be known to a person of ordinary skill in the art. In general, the preparatory reaction vessel or line is similar to the reactor, vessel or line as noted above (noted as the first reaction mixing vessel or mixing line) with respect to the continuous process for reaction of ingenol or the anionic form of ingenol with angelic anhydride or an equivalent angelylating agent. Moreover, the preparatory vessel or line, similar to the reactor, vessel or line, can be provided with means, such as, an agitator or baffles to allow mixing of the reactants.

In another embodiment in accordance with the specification, the reaction of ingenol with a base to form an anionic form of ingenol, as noted above, is not necessarily performed. Rather, ingenol is allowed to react with angelic anhydride or an equivalent angelylating agent. In such an embodiment, the solution containing angelic anhydride or an equivalent angelylating agent can, in one embodiment and for example and without limitation, further contain a base or activating agent. Alternatively, in another embodiment, the base or activating agent can be charged directly, and in a continuous flow, to the first reaction mixing vessel or line for reacting ingenol with angelic anhydride or equivalent angelylating agent.

In the embodiment noted above, where the solution of angelic anhydride or equivalent angelylating agent further contains a base or activating agent, the solution can be prepared by a batch process or a continuous process. The batch process or continuous process can be similar to the batch or continuous process for preparation of a solution of an anionic form of ingenol, as noted above. For instance in one embodiment, for example and without limitation, if the process is carried out as a batch reaction, angelic anhydride or an equivalent angelylating agent can be mixed with the base and/or activating agent in a preparatory vessel, where angelic anhydride or an equivalent angelylating agent can be held or stored till use with reaction with ingenol.

Alternatively, in another embodiment and as noted above, the solution containing angelic anhydride or equivalent angelylating agent containing the base and/or activating agent can be prepared by a continuous process. The continuous process for preparing the solution containing angelic anhydride or equivalent angelylating agent containing the base and/or activating agent is not particularly limited, and can be similar to the continuous process noted above. For example and without limitation, the continuous process can contain the steps of:

charging, in a continuous flow, angelic anhydride or an equivalent angelylating agent to a preparatory reaction vessel or line;

separately charging, in a continuous flow, the base and/or activating agent to the preparatory reaction vessel or line;

permitting the angelic anhydride or an equivalent angelylating agent to mix with the base and/or activating agent to form the solution containing angelic anhydride or an equivalent angelylating agent for charging in the first reaction vessel or line; and discharging, in a continuous flow, the solution containing angelic anhydride or an equivalent angelylating agent from the preparatory reaction vessel or line.

The preparatory reaction vessel or line as used herein is not particularly limited and should be known to a person of ordinary skill in the art. In one embodiment, for example and without limitation, the preparatory reaction vessel or line can be similar to the first reaction vessel or line, as noted above.

Further, in one embodiment, for example and without limitation, the discharge solution containing angelic anhydride or an equivalent angelylating agent from the preparatory reaction vessel or line can be stored prior to use. In another embodiment, for example and without limitation, the discharge solution containing angelic anhydride or an equivalent angelylating agent from the preparatory reaction vessel or line is continuously charged into the first reaction vessel or line for reaction with ingenol or the anionic form of ingenol.

The activating agent used with angelic anhydride or equivalent angelylating agent is not particularly limited and can be determined. The activating agent can be, for example and without limitation, one or more of dicyclohexylcarbodiimide (DCC), N,N'-diisopropylcarbodiimide (DIC), dimethylaminopyridine (DMAP), N-hydroxybenzotriazole (HOBt), N-hydroxysuccinimide (NHS), 1-ethyl-3-(3-dimethylaminopropyl)carbodiimide (EDC), or 1-Hydroxy-7-azabenzotriazole (HOAt). In addition, both the base and activating agent can be used for reaction with ingenol or an anionic form ingenol.

In a still further embodiment, for example and without limitation, the base and/or activating agent as noted above, is not mixed with angelic anhydride or equivalent angelylating agent, rather can be charged using a third line, to the first reaction mixing vessel or mixing line and permit reaction of ingenol or ingenol anion with angelic anhydride or equivalent angelylating agent.

In the continuous process noted above, the concentration of ingenol or anionic form of ingenol in solution is not particularly limited and can depend upon a number of factors, including flow-rate of the solution, equipment size and volume. In one embodiment, for example and without limitation, the concentration of ingenol is selected to maximize the amount of ingenol-3-mebutate formation. In another embodiment, for example and without limitation, the concentration of ingenol or anionic form of ingenol in solution is from about 0.005M to about 0.5M, and all values in between. The concentration of ingenol or anionic form of ingenol in solution is preferably from about 0.01M to about 0.5 M, more preferably from about 0.05M to about 0.25M. The term "about" as used herein is not particularly limited, and can be considered as ±10%.

In addition, the flow-rate of ingenol or anionic form of ingenol in solution is not particularly limited. In one embodiment, for example and without limitation, the flow-rate of ingenol is selected to maximize the amount of ingenol-3-mebutate formation. In another embodiment, for example and without limitation, the flow-rate of ingenol or anionic form of ingenol in solution is from about 1 μL/min to about 10 L/min, and all values in between. The flow rate of ingenol or anionic form of ingenol in solution is preferably from about 100 μL/min to about 1 L/min, and more preferably from about 1 mL/min to about 500 mL/min.

In addition to the above, the concentration of angelic anhydride or equivalent angelylating agent is not particularly limited and can depend upon a number of factors, including concentration of ingenol, flow-rate of the solutions, equipment size and volume. In one embodiment, for example and without limitation, the concentration of angelic anhydride or equivalent angelylating agent is selected to maximize the amount of ingenol-3-mebutate formation. In another embodiment, for example and without limitation, the concentration of angelic anhydride or equivalent angelylating agent in solution is from about 0.005M to about 1M, and all values in between. In a further embodiment, for example and without limitation, the concentration of angelic anhydride or equivalent angelylating agent is preferably from 0.01M to about 0.5 M, and more preferably from about 0.05M to about 0.25M.

The ratio of the concentration of ingenol or anionic form of ingenol to the concentration of angelic anhydride or equivalent angelylating agent is not particularly limited and can be determined. In one embodiment, for example and without limitation, the ratio of the concentration of ingenol or anionic form of ingenol to the concentration of angelic anhydride or equivalent angelylating agent is selected to maximize the amount of ingenol-3-mebutate. In another embodiment, for example and without limitation, the ratio of the concentration of ingenol or anionic form of ingenol to the concentration of angelic anhydride or equivalent angelylating agent is from about 0.5:1 to 1:0.5. In a further embodiment, for example and without limitation, the ratio of the concentration of ingenol or anionic form of ingenol to the concentration of angelic anhydride or equivalent angelylating agent is preferably from about 0.9:1 to 1:0.9, more preferably, from about 0.98:1 to 1:0.98, and most preferably is 1:1.

The ratio of the flow-rate of ingenol or anionic form of ingenol to the flow-rate of angelic anhydride or equivalent angelylating agent is not particularly limited and can be determined. In one embodiment, for example and without limitation, the ratio of the flow-rate of ingenol or anionic form of ingenol to the flow-rate of angelic anhydride or equivalent angelylating agent is selected to maximize the amount of ingenol-3-mebutate. In another embodiment, for example and without limitation, the ratio of the flow-rate of ingenol or anionic form of ingenol to the flow-rate of angelic anhydride or equivalent angelylating agent is from about 0.5:1 to 1:0.5. In a further embodiment, for example and without limitation, the ratio of the flow-rate of ingenol or anionic form of ingenol to the flow-rate of angelic anhydride or equivalent angelylating agent is preferably from about 0.9:1 to 1:0.9, more preferably, from about 0.98:1 to 1:0.98, and most preferably is 1:1.

Further to the above and similar to it, the concentration of base and/or activating agent is not particularly limited and can depend upon a number of factors, including concentration of ingenol, flow-rate of the solutions, equipment size and volume. In one embodiment, for example and without limitation, the concentration of base and/or activating agent is selected to maximize the amount of ingenol-3-mebutate formation. In another embodiment, for example and without limitation, the concentration of base and/or activating agent in solution is from about 0.005M to about 1M, and all values in between. In a further embodiment, for example and without limitation, the concentration of base and/or activating agent is preferably from 0.01M to about 0.5 M, and more preferably from about 0.05M to about 0.25M.

In one embodiment in accordance with the specification, the discharge from the continuous process upon reaction of ingenol or an anionic form of ingenol is quenched using a quenching solution. The method of quenching the reaction is not particularly limited. In a particular embodiment, for example and without limitation, the reaction mixture is charged into a quenching vessel containing a quenching solution. Alternatively, in another embodiment, the quenching solution can be charged subsequently into the quenching vessel, after charging of the reaction mixture.

In a further particular embodiment, the step of quenching the reaction mixture can be performed as continuous process, which can be carried separately from the continuous process for reaction of ingenol or an anionic form of ingenol with angelic anhydride or equivalent angelylating agent. Alternatively, in another embodiment, the step of quenching the reaction mixture can be performed as a continuous process that is in line with (coupled to) and in fluid communication with the continuous process for reaction of ingenol or an anionic form of ingenol with angelic anhydride or equivalent angelylating agent.

The steps for the continuous process for quenching of the reaction mixture are not particularly limited and can be similar to the continuous process steps noted herein. Accordingly, in one embodiment, and for example and without limitation, the process for the continuous process for quenching of the reaction mixture contains the steps of:
  charging, in a continuous flow, the discharged reaction mixture to a quenching vessel or line;
  charging using a quench solution line, in a continuous flow, a quenching solution to the quenching vessel or line;
  permitting mixing of the reaction mixture with the quenching solution to form a quenched reaction mixture; and
  discharging, in a continuous flow, the quenched reaction mixture.

The quenching vessel or line as used herein is not particularly limited and should be known to a person of ordinary skill in the art. In one embodiment, for example and without limitation, the quenching vessel or line can be similar to the first reaction vessel or line, or the preparatory reaction vessel or line, as noted above.

The quenching solution as used herein is not particularly limited. A quenching solution is used for preventing further reaction of the reactants. In one embodiment, for example and without limitation, the quenching solution as used herein contains an acid.

The acid used for quenching of the reaction mixture is not particularly limited and can be determined. In one embodiment, for example and without limitation, the acid is an inorganic or organic acid. Inorganic acids are preferred and can include, for example and without limitation, hydrochloric acid, sulfuric acid, phosphoric acid and hydrobromic acid. In a particular embodiment, for example and without limitation, the acid used is hydrochloric acid.

The concentration of the acid used for quenching the reaction is not particularly limited and can be determined. In one embodiment, for example and without limitation, the concentration of the acid is selected to allow quenching of the reaction mixture while minimizing any product degradation or formation of impurities. In another embodiment, for example and without limitation, the concentration of the acid is from about 0.005M to about 1M, and all values in between. In a further embodiment, for example and without limitation, the concentration of the acid is preferably from about 0.01M to about 0.5 M, and more preferably from about 0.05M to about 0.25M.

The ratio of the concentration of discharged reaction mixture to the concentration of quenching solution is not particularly limited and can be determined. In one embodiment, for example and without limitation, the ratio of the concentration of discharged reaction mixture to the concentration of quenching solution is selected to maximize the amount of ingenol-3-mebutate. In another embodiment, for example and without limitation, the ratio of the concentration of discharged reaction mixture to the concentration of quenching solution is from about 0.5:1 to 1:0.5. In a further embodiment, for example and without limitation, the ratio of the concentration of discharged reaction mixture to the concentration of quenching solution is preferably from about 0.9:1 to 1:0.9, more preferably, from about 0.98:1 to 1:0.98, and most preferably is 1:1.

The ratio of the flow-rate of reaction mixture to the flow-rate of acid is not particularly limited and can be determined. In one embodiment, for example and without limitation, the ratio of the flow-rate of reaction mixture to the flow-rate of acid is selected to maximize the amount of ingenol-3-mebutate. In one embodiment, for example and without limitation, the ratio of the flow-rate of ingenol or anionic form of ingenol to the flow-rate of angelic anhydride or equivalent angelylating agent is selected to maximize the amount of ingenol-3-mebutate. In another embodiment, for example and without limitation, the ratio of the flow-rate of the discharged reaction solution to the flow-rate of the quenching solution is from about 0.5:1 to 1:0.5. In a further embodiment, for example and without limitation, the ratio of the flow-rate of the discharged reaction solution to the flow-rate of the quenching solution is preferably from about 0.9:1 to 1:0.9, more preferably, from about 0.98:1 to 1:0.98, and most preferably is 1:1.

Upon completion of the reaction, ingenol-3-mebutate is formed along with a number of regioisomers (as shown in Scheme 1 above), including: ingenol-5-mebutate, ingenol-20-mebutate and ingenol-3,20-mebutate. Ingenol-3-mebutate can then be separated from the other regioisomers (ingenol-5-mebutate, ingenol-20-mebutate and ingenol-3, 20-mebutate). The method of separation and/or purification of ingenol-3-mebutate is not particularly limited. In one embodiment, for example and without limitation, ingenol-3-mebutate is separated and purified by chromatography or crystallization.

In one embodiment, in accordance with the disclosure herein, the other regioisomers (ingenol-5-mebutate, ingenol-20-mebutate and ingenol-3,20-mebutate) can be pooled for re-cycling. This can be achieved by, for example and without limitation, by combining the other regioisomers and per-forming a hydrolysis reaction to form ingenol, which can then be used in the continuous process disclosed herein. This can allow for improvement of the throughput and overall yield of ingenol-3-angelate.

The method of carrying out the hydrolysis reaction is not particularly limited and can be determined. In one embodiment, for example and without limitation, the hydrolysis reaction involves cleavage of the ester bond in ingenol-5-mebutate, ingenol-20-mebutate and ingenol-3,20-mebutate to form ingenol (Scheme 2). The reagent(s) used for carrying out the hydrolysis is not particularly limited and can be determined. In one embodiment, for example and without limitation, the hydrolysis reaction is carried out by base hydrolysis.

Scheme 2: Hydrolysis of other reaction products to form ingenol.

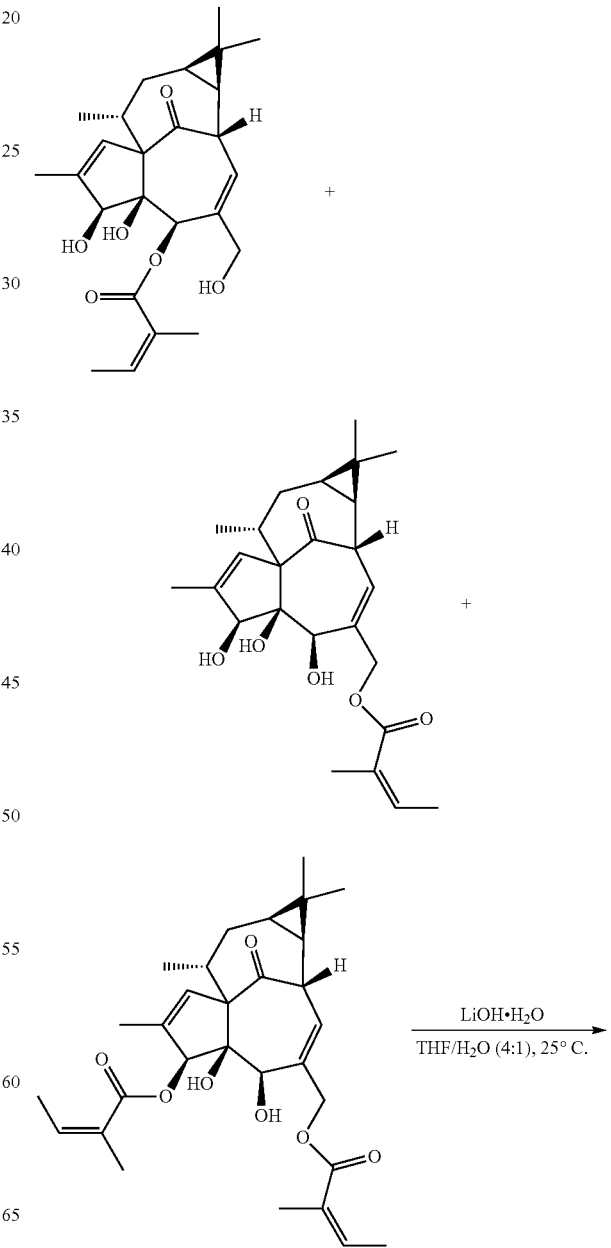

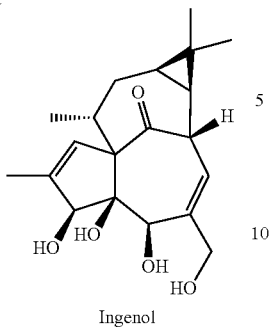

Ingenol

The base used for carrying out the hydrolysis reaction of ingenol-5-mebutate, ingenol-20-mebutate and ingenol-3,20-mebutate is not particularly limited and can be determined. In one embodiment, for example and without limitation, the base is an organic or inorganic base in an aqueous medium (contains water). In a further embodiment, for example and without limitation, the base is sodium hydroxide, lithium hydroxide, potassium hydroxide, or any of the bases noted above in an aqueous medium to permit formation of hydroxide ions, for hydrolysis of the ester bond in the other products.

EXAMPLES

The following examples are illustrative and non-limiting and represent specific embodiments of the present invention.

Reference Example 1

Initially, batch reactions were carried out for a one-step synthesis of ingenol-3-mebutate, starting from ingenol and using conditions similar to those disclosed in Scheme 1 (and reproduced herein below for convenience).

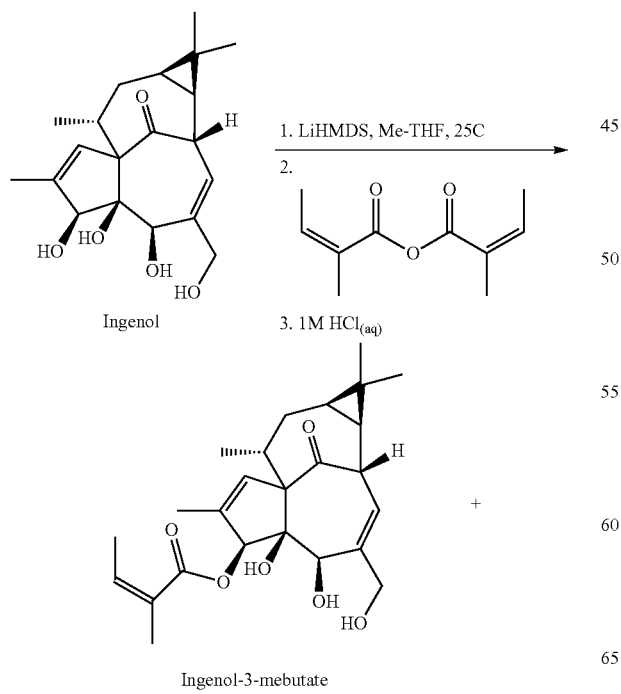

Ingenol-3-mebutate

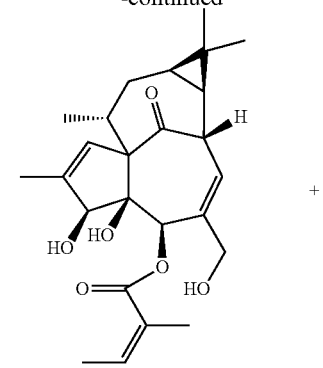

Ingenol-5-mebutate

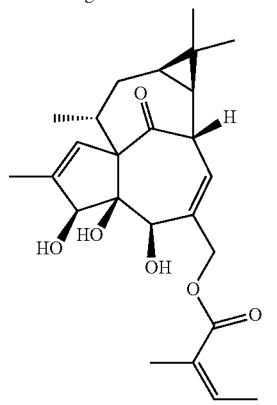

Ingenol-20-mebutate

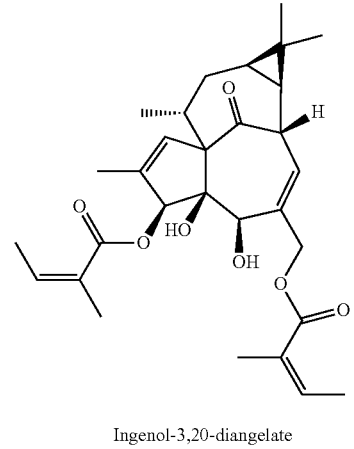 [SMILES: C/C=C(/C)C(=O)OCC1=C[C@@H]2C(=O)C3(C=C(C)[C@H](OC(=O)/C(C)=C\C)[C@@]3(O)[C@@H]1O)[C@H](C)C[C@@H]1[C@H]2C1(C)C]

Ingenol-3,20-diangelate

There are three reactive hydroxyl groups at C-3, C-5 and C-20 that can undergo angeloylation. Evidence for reaction at the C-4 tertiary hydroxyl group is not mentioned in literature, presumably due to the steric environment and therefore can be considered as being a much less reactive. Theoretically speaking, three reactive hydroxyl groups should give ~33% of each isomer if all three hydroxyl groups were assumed to be identical. However, the hydroxyl groups at C-3 and C-5 of ingenol are secondary and the hydroxyl group at C-20 is primary. Given the structural geometry and complexity of ingenol, a difference in the reactivity of the three hydroxyl groups can be expected. Furthermore, primary hydroxyl groups are typically more reactive and the angeloylation at C-20 would be expected to be dominant.

The results of the initials trials are highlighted in Table 1. Samples were analysed by UPLC using an Acquity UPLC HSS C18 SB column and acetonitrile/water as eluent. Without modifying the existing conditions (Liang, X. et al. Synlett 2012, 23, 2647), the desired product, ingenol-3-mebutate, was observed with the isomer ingenol-20-mebutate being the major product in the reaction mixture (entry 1). Modification of the reaction conditions such that the introduction of angelic anhydride was done sequentially as described in entries 2-4, showed a positive impact resulting in a greater abundance of ingenol-3-mebutate relative to ingenol-20-mebutate. However, a major, less polar impurity was observed in these trials which was believed to be the diangelate (ingenol-3,20-mebutate) resulting from double angeloylation at C-3 and C-20.

TABLE 1

Results of batch reaction for the one-step synthesis of ingenol-3-mebutate.

| | | | UPLC (% a/a) Analysis | | | | |
|---|---|---|---|---|---|---|---|
| Trial | Ingenol | Conditions | Ingen | C-5 | C-20 | C-3 | C-3,20 |
| 1 | 101 mg | 1. Charged ingenol, anhydride and THF, cooled to 10° C. 2. LiHMDS (1.2 eq), 10° C., 2-3 min 3. Warmed to 25° C. (25 min) and quenched with $H_2O$ | 18.67 | 2.02 | 38.05 | 11.01 | 20.98 |
| 2 | 99 mg | 1. Charged ingenol and THF, cooled to 10° C. 2. LiHMDS (1.2 eq), 10° C., 5 min 3. Anhydride (1.2 eq) in THF, 10° C., 2 min 4. Warmed to 25° C. (20 min) and quenched with $H_2O$ | 12.74 | 1.70 | 16.62 | 15.57 | 43.21 |
| 3 | 98 mg | 1. Charged ingenol and THF, cooled to −10° C. 2. LiHMDS (1.2 eq), −10° C., 2 min 3. Anhydride (1.2 eq) in THF 10° C., 10 min 4. Warmed to 5° C. (10 min) quenched with $H_2O$ | 7.00 | 2.60 | 19.43 | 24.71 | 36.74 |
| 4 | 103 mg | Repeat of Trial #2 with 1M $HCl_{(aq)}$ quench after 10 min stirring at 25° C. | 9.96 | 1.35 | 20.97 | 23.97 | 33.06 |

Ingen: ingenol;
C-5: ingenol-5-mebutate;
C-20: ingenol-20-mebutate;
C-3: ingenol-3-mebutate;
C-3,20: ingenol-3,20-mebutate;

Additional trials were conducted at larger scale and the results of those batch processing trials are shown in Table 2.

TABLE 2

Additional results of batch reaction for the one-step synthesis of ingenol-3-mebutate.

| | | | UPLC (% a/a) IPC Data | | | | |
|---|---|---|---|---|---|---|---|
| Trial | Ingenol | Conditions | Ingen | C-5 | C-20 | C-3 | C-3,20 |
| 1 | 513 mg | 1. LiHMDS (1.02 eq), Me-THF, 10° C. added to ingenol (1.02 eq). 2. Angelic anhydride (1.02 eq), Me-THF, 10 to 25° C. | 12.48 | 2.58 | 23.99 | 30.70 | 22.12 |
| 2 | 523 mg | 1. Ingenol (1.0 eq), angelic anhydride (1.05 eq), Me-THF, −78° C. 2. LiHMDS (1.05 eq), −78° C. | 18.47 | 1.06 | 25.09 | 24.82 | 25.13 |

TABLE 2-continued

Additional results of batch reaction for the one-step synthesis of ingenol-3-mebutate.

| | | | UPLC (% a/a) IPC Data | | | | |
|---|---|---|---|---|---|---|---|
| Trial | Ingenol | Conditions | Ingen | C-5 | C-20 | C-3 | C-3,20 |
| 3 | 1.00 g | 1. Ingenol (1.0 eq), angelic anhydride (1.05 eq), Me-THF, −78° C.<br>2. LiHMDS (1.05 eq), −78° C. | 28.66 | 0.39 | 14.74 | 22.66 | 20.21 |

Ingen: ingenol;
C-5: ingenol-5-mebutate;
C-20: ingenol-20-mebutate;
C-3: ingenol-3-mebutate;
C-3,20: ingenol-3,20-mebutate;

The results described in Table 2 represent the variability observed with typical batch processing. As well, the ratio of ingenol-3-angelate to the isomers/impurities typically observed varies unfavourably amongst the trials. These results suggest that reproducibility may be an issue which could be further complicated as the scale increases.

Reference Example 2

Solvent Screening

Reactions to maximize ingenol-3-mebutate formation were pursued first by conducting a solvent screen. As shown in Table 3, 2-Me-THF (Me-THF) appeared to give a better selectivity towards the desired C-3 hydroxyl group relative to THF or toluene when using the method for Trial 2, Table 1. Solubility issues were observed with toluene initially but complete dissolution occurred with the addition of LiHMDS. Based on these experiments, 2-Me-THF was selected for further development.

Example 3

Continuous Flow Reaction for Preparation of Ingenol-3-Mebutate

A three line microreactor cell was used with the lithiation of ingenol conducted externally. The parameters investigated for the angeloylation of ingenol using the continuous flow microreactor are displayed in Table 4. The study focused on the proof of concept by varying temperature and flow rates to maximize the selectivity, impurity formation, and conversion.

TABLE 3

Results of batch reaction for solvent screening

| | | | UPLC (% a/a) Analysis | | | | |
|---|---|---|---|---|---|---|---|
| Trial | Ingenol | Conditions | Ingen | C-5 | C-20 | C-3 | C-3,20 |
| 1 | 104 mg | 1. Charged ingenol and PhCH$_3$, cooled to 10° C.<br>2. LiHMDS (1.2 eq), 10° C., 2 min<br>3. Anhydride (1.2 eq) in PhCH$_3$, 10° C., 5 min<br>4. Warmed to 25° C. (15 min) and quenched with 1M HCl$_{(aq)}$ | 3.82 | 0.10 | 9.94 | 5.33 | 16.31* |
| 2 | 98 g | 1. Charged ingenol and Me-THF, cooled to 10° C.<br>2. LiHMDS (1.2 eq), 10° C., 2 min<br>3. Anhydride (1.2 eq) in Me-THF, 10° C., 5 min<br>4. Warmed to 25° C. (15 min) and quenched with 1M HCl$_{(aq)}$ | 7.67 | 0.27 | 9.81 | 17.39 | 29.55 |
| 3 | 99 mg | 1. Charged ingenol and THF, cooled to 10° C.<br>2 LiHMDS (1.2 eq), THF, 10° C., 5 min<br>3. Anhydride (1.2 eq) in THF, 10° C., 2 min<br>4. Warmed to 25° C. (20 min) and quenched with H$_2$O | 12.74 | 1.70 | 16.62 | 15.57 | 43.21 |

*Integrated with peak possibly corresponding to toluene.

TABLE 4

Investigation of a continuous flow reaction for preparation of Ingenol-3-mebutate

| Trial* | Line A | B | C | Temp (° C.) | Flow (μL/min) A | B | C |
|---|---|---|---|---|---|---|---|
| 1 | Lithiated | Angelic | 1M | 22 | 25 | 25 | 30 |
| 2 | ingenol | anhydride | HCl | 10 | 25 | 25 | 30 |
| 3 | in Me-THF | in Me-THF | (aq) | 0 | 25 | 25 | 30 |
| 4 | 0.25M | 0.25M | | −10 | 25 | 25 | 30 |
| 5 | | | | 22 | 13 | 13 | 15 |
| 6 | | | | 10 | 13 | 13 | 15 |
| 7 | | | | 0 | 13 | 13 | 15 |
| 8 | | | | −10 | 13 | 13 | 15 |
| 9 | | | | 10 | 13 | 15 | 15 |
| 10 | | | | 10 | 13 | 18 | 15 |

*Conducted using a Chemtrix, Labtrix model continuous flow reactor with microreactor cell #3223

Surprisingly, as illustrated in Table 5, the ingenol-3-mebutate was observed to be the major product in all trials. As well, the double angeloylation impurity (ingenol-3,20-mebutate) was significantly reduced relative to the results listed in Tables 1 and 2, where batch processes were followed. In all cases, there remained some unreacted ingenol. The regioisomers (ingenol-5-mebutate and ingenol-20-mebutate) were rather consistent throughout all of the runs with slight reductions as the temperature was lowered. In addition, the continuous flow shows a consistent profile over the parameters investigated. Samples were analysed by HPLC using a Sunfire C18 column and acetonitrile/water as eluent.

TABLE 5

HPLC Data for the continuous flow reaction for preparation of Ingenol-3-mebutate

| Trial | Ingenol RRT = 0.27 | C-5 RRT = 0.71 | C-20 RRT = 0.85 | C-3 RRT = 1.0 | C-3,20 RRT = 1.75 |
|---|---|---|---|---|---|
| 1 | 20.09 | 0.32 | 24.37 | 33.90 | 9.73 |
| 2 | 20.89 | 0.26 | 23.17 | 34.77 | 8.90 |
| 3 | 21.49 | 0.22 | 21.70 | 34.20 | 9.41 |
| 4 | 24.08 | 0.20 | 20.63 | 33.54 | 7.24 |
| 5 | 17.68 | 0.34 | 23.54 | 32.96 | 13.37 |
| 6 | 17.96 | 0.28 | 22.19 | 33.98 | 12.18 |
| 7 | 18.28 | 0.15 | 21.04 | 33.58 | 11.43 |
| 8 | 19.36 | 0.15 | 19.98 | 32.97 | 10.47 |
| 9 | 16.47 | 0.20 | 20.91 | 32.11 | 13.88 |
| 10 | 15.99 | 0.21 | 20.44 | 31.42 | 13.50 |

Ingen: ingenol; C-5: ingenol-5-mebutate; C-20: ingenol-20-mebutate; C-3: ingenol-3-mebutate; C-3,20: ingenol-3,20-mebutate;

The use of a continuous flow microreactor demonstrates that the reaction could be controlled, affording ingenol-3-mebutate as the major isomer. Ingenol-3-mebutate could be purified by chromatography and precipitation/trituration.

Example 4

Additional Continuous Flow Reactions for Preparation of Ingenol-3-Mebutate

The use of a continuous flow process for the direct conversion of ingenol to ingenol-3-angelate was further investigated as described in Table 6. The results outlined in Table 7 correspond directly to the trials outlined in Table 6. The HPLC data refers to the direct analysis of the reaction mixtures.

TABLE 6

Continuous Flow Process Investigation using a Chemtrix Microreactor

| Trial* | Line A | B | C | Temp (° C.) | Flow (μL/min) A | B | C |
|---|---|---|---|---|---|---|---|
| 1 | lithiated | Angelic | 1M | 10 | 5 | 5 | 2.5 |
| 2 | ingenol | anhydride | HCl$_{(aq)}$ | 0 | 5 | 5 | 2.5 |
| 3 | in Me-THF | in Me-THF | | 0 | 3 | 3 | 1.5 |
| 4 | 0.05M | 0.05M | | −10 | 5 | 5 | 2.5 |
| 5 | | | | −10 | 3 | 3 | 1.5 |

*Conducted using a Chemtrix, Labtrix model continuous flow reactor with microreactor cell #3223

TABLE 7

HPLC Data for the Continuous Flow Process Investigation

| | HPLC (% a/a) | | | | |
|---|---|---|---|---|---|
| Trial | Ingenol RRT = 0.24 | Ingenol-5-angelate RRT= 0.71 | Ingenol-20-angelate RRT = 0.89 | Ingenol-3-angelate RRT = 1.0 | Ingenol-3,20-diangelate RRT = 1.90 |
| 1 | 18.38 | n.d. | 14.13 | 39.76 | 22.25 |
| 2 | 16.90 | n.d. | 14.26 | 40.72 | 23.20 |
| 3 | 17.91 | n.d. | 14.98 | 40.33 | 23.36 |
| 4 | 20.87 | n.d. | 14.47 | 39.82 | 20.74 |
| 5 | 19.02 | n.d | 14.92 | 39.79 | 21.74 |

Based on the results shown in Table 7, the reaction was scaled-up using the continuous flow conditions for entry 2 of Table 6. The results for this scale-up are listed below in Table 8.

TABLE 8

HPLC Data for the Continuous Flow Scale-up of Optimized Conditions

| | | HPLC (% a/a) | | | |
|---|---|---|---|---|---|
| Trial | Input Mass of Ingenol (mg) | Ingenol RRT = 0.24 | Ingenol-5-angelate RRT = 0.71 | Ingenol-20-angelate RRT = 0.89 | Ingenol-3-angelate RRT = 1.0 | Ingenol-3,20-diangelate RRT = 1.90 |
| 1 | 24 mg | 18.88 | n.d. | 15.41 | 39.37 | 23.17 |

The scaled-up reaction mixture was purified first by aqueous work-up followed by silica gel purification using a Biotage (KP-Sil cartridge) to provide ingenol-3-angelate in 40% yield and >95% (a/a) purity by HPLC (Fraction 2, Table 9). The first eluting fractions were isolated as a mixture predominately enriched with the impurities ingenol-20-angelate and the diangelate ingenol-3,20-diangelate (Fraction 1, Table 9). Unreacted ingenol was recovered in the third fraction, representing a recovery yield of ~29% (fraction 3, Table 9).

TABLE 9

HPLC Data for the Biotage Purification

| | | HPLC (% a/a) | | | |
|---|---|---|---|---|---|
| Fraction | Mass/ Yield | Ingenol RRT = 0.24 | Ingenol-5-angelate RRT = 0.71 | Ingenol-20-angelate RRT = 0.89 | Ingenol-3-angelate RRT = 1.0 | Ingenol-3,20-diangelate RRT = 1.90 |
| 1 | 7.0 mg | n.d. | n.d. | 45.68 | 5.65 | 46.80 |
| 2 | 11.5 mg, 40% | n.d | n.d. | 3.36 | 95.42 | 0.10 |
| 3 | 7.0 mg, 29% | 97.71 | n.d. | 0.16 | 0.27 | n.d. |

Example 5

Recycling of Angeloylated Ingenol Derivatives to Ingenol

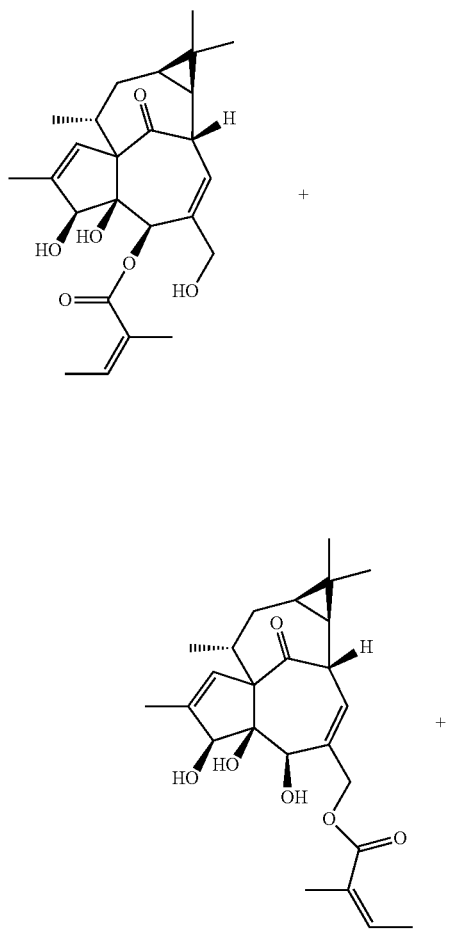

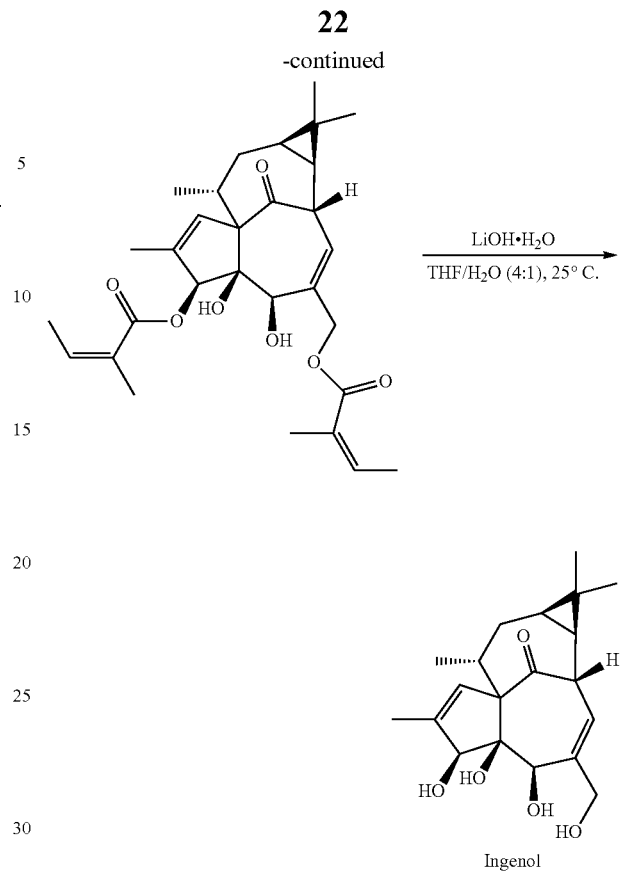

Ingenol

Fraction 1, from Table 9 was subjected to the basic recycling conditions and the reaction progress was monitored by HPLC for the appearance of ingenol and disappearance of ingenol-20-angelate and ingenol-3,20-diangelate. Once the reaction was deemed complete, the material was isolated by aqueous workup for consolidation with fraction 3, Table 9, in order to conduct another continuous flow reaction using the optimized conditions. The results of the base-catalyzed hydrolysis are outlined in Table 10.

TABLE 10

Base-Catalyzed Hydrolysis of Impurities to Recover Ingenol

| | | | HPLC (% a/a) | | | |
|---|---|---|---|---|---|---|
| Input Mass (mg) | Reaction Conditions | Isolated Mass (mg) | Ingenol RRT = 0.24 | Ingenol-20-angelate RRT = 0.89 | Ingenol-3-angelate RRT = 1.0 | Ingenol-3,20-diangelate RRT = 1.90 |
| 7.0 | LiOH-1-120, 25-40° C., THF:H20 (4:1) | 2.0 | 71.94 | 1.0 | n.d. | 1.92 |

The continuous flow conditions (Trial 2, Table 6) were conducted on the ingenol recovered in Table 10 and fraction 3 of Table 9. The results are displayed in Table 11.

TABLE 11

HPLC Data for the Continuous Flow of Recycled Ingenol

| Input | HPLC (% a/a) | | | | |
|---|---|---|---|---|---|
| Mass of Recovered Ingenol (mg) | Ingenol RRT = 0.27 | Ingenol-5-angelate RRT = 0.71 | Ingenol-20-angelate RRT = 0.85 | Ingenol-3-angelate RRT = 1.0 | Ingenol-3,20-diangelate RRT = 1.75 |
| 9.0 (crude) | 11.90 | n.d. | 14.31 | 28.33 | 40.69 |

It was shown that a continuous flow process for the one-step conversion of ingenol to ingenol-3-angelate presents a better manufacturing process route than with standard batch style processing providing better selectivity in favor of the desired isomer and allowing recycling of undesired isomers into the product.

EMBODIMENTS

1. A continuous process for preparation of ingenol-3-angelate, comprising:
   charging using a first line, in a continuous flow, a solution containing ingenol or ingenol anion to a first reaction mixing vessel or mixing line;
   charging using a second line, in a continuous flow, a solution containing angelic anhydride, or an equivalent angelylating agent to a first reaction mixing vessel or mixing line;
   permitting reaction of ingenol or ingenol anion with angelic anhydride, or an equivalent angelylating agent in the first reaction mixing vessel or mixing line to form a reaction mixture containing ingenol-3-mebutate; and
   discharging, in a continuous flow, the reaction mixture from the first reaction mixing vessel or mixing line for quenching the reaction mixture.

2. The continuous process according to embodiment 1, wherein the solution containing ingenol or ingenol anion is formed by reacting ingenol with a base.

3. The continuous process according to embodiment 2, wherein the step of reacting ingenol with the base is performed in a batch reaction or a preliminary continuous process.

4. The continuous process according to embodiment 3, wherein the batch reaction is performed by mixing ingenol and the base in a preparatory vessel.

5. The continuous process according to embodiment 3, wherein the preliminary continuous process comprises the step of:
   charging, in a continuous flow, ingenol to a preparatory reaction vessel or line;
   separately charging, in a continuous flow, the base to the preparatory reaction vessel or line;
   permitting the ingenol to mix and/or react with the base to form the solution containing ingenol or ingenol anion; and
   discharging, in a continuous flow, the solution containing ingenol or ingenol anion from the preparatory reaction vessel or line.

6. The continuous process according to embodiment 5, wherein the discharge from the preparatory reaction vessel or line is charged, in a continuous flow, to the first reaction mixing vessel or mixing line.

7. The continuous process according to embodiment 1, wherein the solution containing angelic anhydride, or an equivalent angelylating agent further comprises a base and/or an activating agent.

8. The continuous process according to embodiment 7, wherein the solution containing angelic anhydride, or an equivalent angelylating agent and the base and/or the activating agent is prepared in a batch reactor or in a preliminary continuous process.

9. The continuous process according to 8, wherein the preparation in the batch reaction is performed by mixing angelic anhydride, or an equivalent angelylating agent and the base and/or activating agent in a preparatory vessel.

10. The continuous process according to embodiment 8, wherein the preliminary continuous process comprises the step of:
    charging, in a continuous flow, angelic anhydride, or an equivalent angelylating agent to a preparatory reaction vessel or line;
    separately charging, in a continuous flow, the base and/or activating agent to the preparatory reaction vessel or line;
    permitting the angelic anhydride, or an equivalent angelylating agent to mix with the base and/or activating agent to form the solution containing angelic anhydride, or an equivalent angelylating agent for charging in the first reaction vessel; and
    discharging, in a continuous flow, the solution containing angelic anhydride, or an equivalent angelylating agent from the preparatory reaction vessel or line.

11. The continuous process according to embodiment 10, wherein the discharge from the preparatory reaction vessel or line is charged, in a continuous flow, to the first reaction mixing vessel or mixing line.

12. The continuous process according to embodiment 1, further comprising:
    charging using a third line, in a continuous flow, a base and/or activating agent to the first reaction mixing vessel or mixing line; and
    permitting reaction of ingenol or ingenol anion with angelic anhydride, or an equivalent angelylating agent in the presence of the base and/or activating agent in the first reaction mixing vessel or mixing line to form a reaction mixture containing ingenol-3-mebutate.

13. The continuous process according to any one of embodiments 7 to 12, wherein the activating agent is one or more of dicyclohexylcarbodiimide (DCC), N,N'-diisopropylcarbodiimide (DIC), dimethylaminopyridine (DMAP), N-hydroxybenzotriazole (HOBt), N-hydroxysuccinimide (NHS), 1-ethyl-3-(3-dimethylaminopropyl)carbodiimide (EDC), or 1-Hydroxy-7-azabenzotriazole (HOAt).

14. The continuous process according to any one of embodiments 2 to 13, wherein the base is sodium hydride, lithium hydride, butyl lithium (Bu-Li), tert-butyl lithium (t-BuLi), butyl potassium (BuK), lithium hexamethyl disilazane (LiHMDS) ($C_6H_{18}LiNSi_2$), 2,2,6,6-tetramethylpiperidine, sodium bis(trimethylsilyl)amide ($C_6H_{18}NNaSi_2$), sodium amide ($NaNH_2$), potassium bis(trimethylsilyl)amide ($C_6H_{18}KNSi_2$), triethylamine, pyridine, imidazole, piperidine, 2,6-lutidine, lithium dimethylamide ($C_2H_6LiN$), Lithium diisopropylamide ($C_6H_{14}LiN$), Lithium diethylamide ($C_4H_{10}LiN$), Lithium dicyclohexylamide ($C_{12}H_{22}LiN$), diisopropylethylamine (DIPEA), ethylamine, 4-(dimethylamino)pyridine, or Dabco®.

15. The continuous process according to any one of embodiments 1 to 14, wherein the concentration of ingenol or ingenol anion in solution is from about 0.005M to about 0.5M.

16. The continuous process according to any one of embodiments 1 to 15, wherein the concentration of angelic anhydride, or an equivalent angelylating agent in solution is from about 0.005M to about 1M.

17. The continuous process according to any one of embodiments 1 to 16, wherein the concentration of the base and/or activating agent in solution is from about 0.005M to about 1M.

18. The continuous process according to any one of embodiments 1 to 16, wherein the flow-rate of ingenol or ingenol anion in solution is from about 1 µL/min to about 10 L/min.

19. The continuous process according to any one of embodiments 1 to 18, wherein the concentration of ingenol or ingenol anion in solution to the concentration of angelic anhydride, or an equivalent angelylating agent in solution is from about 0.5:1, 0.6:1, 0.7:1, 0.8:1, 0.9:1, 0.95:1, 0.97:1, 0.98:1, 0.99:1, 1:1, 1:0.99, 1:0.98, 1.:0.97, 1:0.95, 1:0.9, 1:0.8, 1:0.7, 1:0.6, or 1:0.5.

20. The continuous process according to any one of embodiments 1 to 19, wherein the flow-rate of the solution containing ingenol or ingenol anion to the flow-rate of the solution containing angelic anhydride, or an equivalent angelylating agent is from about 0.5:1, 0.6:1, 0.7:1, 0.8:1, 0.9:1, 0.95:1, 0.97:1, 0.98:1, 0.99:1, 1:1, 1:0.99, 1:0.98, 1.:0.97, 1:0.95, 1:0.9, 1:0.8, 1:0.7, 1:0.6, or 1:0.5.

21. The continuous process according to any one of embodiments 1 to 20, wherein the reaction mixture is discharged into a quenching vessel containing a quenching solution.

22. The continuous process according to any one of embodiments 1 to 21, wherein the reaction mixture is discharged into a quenching vessel, and further comprising charging a quenching solution to the quenching vessel.

23. The continuous process according to any one of embodiments 1 to 20, further comprising:
charging, in a continuous flow, the discharged reaction mixture to a quenching vessel or line;
charging using a quench solution line, in a continuous flow, a quenching solution to the quenching vessel or line;
permitting mixing of the reaction mixture with the quenching solution to form a quenched reaction mixture; and
discharging, in a continuous flow, the quenched reaction mixture.

24. The continuous process according to any one of embodiments 21 to 23, wherein the quenching solution comprises an acid.

25. The continuous process according to embodiment 24, wherein the acid is HCl, $H_2SO_4$, $H_3PO_4$, acetic acid, lactic acid, or formic acid.

26. The continuous process according to any one of embodiments 21 to 25, wherein the concentration of discharged reaction mixture to the concentration of quenching solution is from about 1:20, 1:15, 1:10, 1:5, 1:4, 1:3, 1:2, or 1:1.

27. The continuous process according to any one of embodiments 21 to 26, wherein the flow-rate of the discharged reaction solution to the flow-rate of the quenching solution is from about 0.5:1, 0.6:1, 0.7:1, 0.8:1, 0.9:1, 0.95:1, 0.97:1, 0.98:1, 0.99:1, 1:1, 1:0.99, 1:0.98, 1.:0.97, 1:0.95, 1:0.9, 1:0.8, 1:0.7, 1:0.6, or 1:0.5.

28. The continuous process according to any one of embodiments 21 to 27, further comprising purifying the quenched reaction mixture to separate ingenol-3-mebutate from other reaction products.

29. The continuous process according to embodiment 28, further comprising hydrolysis of the other reaction products to obtain ingenol.

30. The continuous process according to embodiment 29, further comprising recycling ingenol obtained from the hydrolysis reaction of the other reaction products in the continuous process for forming ingenol-3-mebutate.

Certain adaptations and modifications of the described embodiments can be made. Therefore, the above discussed embodiments are considered to be illustrative and not restrictive.

What is claimed is:

1. A continuous process for preparation of ingenol-3-angelate, comprising:
charging using a first line, in a continuous flow, a solution containing ingenol or ingenol anion to a first reaction mixing vessel or mixing line;
charging using a second line, in a continuous flow, a solution containing angelic anhydride, or an equivalent angelylating agent to a first reaction mixing vessel or mixing line;
permitting reaction of ingenol or ingenol anion with angelic anhydride, or an equivalent angelylating agent in the first reaction mixing vessel or mixing line to form a reaction mixture containing ingenol-3-mebutate; and
discharging, in a continuous flow, the reaction mixture from the first reaction mixing vessel or mixing line for quenching the reaction mixture.

2. The continuous process according to claim 1, wherein the solution containing ingenol or ingenol anion is formed by reacting ingenol with a base.

3. The continuous process according to claim 2, wherein the step of reacting ingenol with the base is performed in a batch reaction or a preliminary continuous process.

4. The continuous process according to claim 3, wherein the batch reaction is performed by mixing ingenol and the base in a preparatory vessel.

5. The continuous process according to claim 3, wherein the preliminary continuous process comprises the step of:
charging, in a continuous flow, ingenol to a preparatory reaction vessel or line;
separately charging, in a continuous flow, the base to the preparatory reaction vessel or line;
permitting the ingenol to mix and/or react with the base to form the solution containing ingenol or ingenol anion; and
discharging, in a continuous flow, the solution containing ingenol or ingenol anion from the preparatory reaction vessel or line.

6. The continuous process according to claim 5, wherein the discharge from the preparatory reaction vessel or line is charged, in a continuous flow, to the first reaction mixing vessel or mixing line.

7. The continuous process according to claim 1, wherein the solution containing angelic anhydride, or an equivalent angelylating agent further comprises a base and/or an activating agent.

8. The continuous process according to claim 7, wherein the solution containing angelic anhydride, or an equivalent angelylating agent and the base and/or the activating agent is prepared in a batch reactor or in a preliminary continuous process.

9. The continuous process according to claim 8, wherein the preliminary continuous process comprises the step of:
charging, in a continuous flow, angelic anhydride, or an equivalent angelylating agent to a preparatory reaction vessel or line;
separately charging, in a continuous flow, the base and/or activating agent to the preparatory reaction vessel or line;
permitting the angelic anhydride, or an equivalent angelylating agent to mix with the base and/or activating agent to form the solution containing angelic anhydride, or an equivalent angelylating agent for charging in the first reaction vessel; and
discharging, in a continuous flow, the solution containing angelic anhydride, or an equivalent angelylating agent from the preparatory reaction vessel or line.

10. The continuous process according to claim 1, further comprising:
charging using a third line, in a continuous flow, a base and/or activating agent to the first reaction mixing vessel or mixing line; and
permitting reaction of ingenol or ingenol anion with angelic anhydride, or an equivalent angelylating agent in the presence of the base and/or activating agent in the first reaction mixing vessel or mixing line to form a reaction mixture containing ingenol-3-mebutate.

11. The continuous process according to claim 7, wherein the activating agent is one or more of dicyclohexylcarbodiimide (DCC), N,N'-diisopropylcarbodiimide (DIC), dimethylaminopyridine (DMAP), N-hydroxybenzotriazole (HOBt), N-hydroxysuccinimide (NHS), 1-ethyl-3-(3-dimethylaminopropyl)carbodiimide (EDC), or 1-Hydroxy-7-azabenzotriazole (HOAt).

12. The continuous process according to claim 2, wherein the base is sodium hydride, lithium hydride, butyl lithium (Bu-Li), tert-butyl lithium (t-BuLi), butyl potassium (BuK), lithium hexamethyl disilazane (LiHMDS) ($C_6H_{18}LiNSi_2$), 2,2,6,6-tetramethylpiperidine, sodium bis(trimethylsilyl)amide ($C_6H_{18}NNaSi_2$), sodium amide ($NaNH_2$), potassium bis(trimethylsilyl)amide ($C_6H_{18}KNSi_2$), triethylamine, pyridine, imidazole, piperidine, 2,6-lutidine, lithium dimethylamide ($C_2H_6LiN$), Lithium diisopropylamide ($C_6H_{14}LiN$), Lithium diethylamide ($C_4H_{10}LiN$), Lithium dicyclohexylamide ($C_{12}H_{22}LiN$), diisopropylethylamine (DIPEA), ethylamine, 4-(dimethylamino)pyridine, or Dabco®.

13. The continuous process according to claim 1, wherein the concentration of ingenol or ingenol anion in solution is from about 0.005M to about 0.5M.

14. The continuous process according to claim 1, wherein the concentration of ingenol or ingenol anion in solution to the concentration of angelic anhydride, or an equivalent angelylating agent in solution is from about 0.5:1 to 1:0.5.

15. The continuous process according to claim 1, wherein the reaction mixture is discharged into a quenching vessel containing a quenching solution.

16. The continuous process according to claim 1, further comprising:
charging, in a continuous flow, the discharged reaction mixture to a quenching vessel or line;
charging using a quench solution line, in a continuous flow, a quenching solution to the quenching vessel or line;
permitting mixing of the reaction mixture with the quenching solution to form a quenched reaction mixture; and
discharging, in a continuous flow, the quenched reaction mixture.

17. The continuous process according to claim 15, wherein the quenching solution comprises an acid.

18. The continuous process according to claim 17, wherein the acid is HCl, $H_2SO_4$, $H_3PO_4$, acetic acid, lactic acid, or formic acid.

19. The continuous process according to claim 15, wherein the concentration of discharged reaction mixture to the concentration of quenching solution is from about 1:20 to 1:1.

20. The continuous process according to claim 15, further comprising purifying the quenched reaction mixture to separate ingenol-3-mebutate from other reaction products.

21. The continuous process according to claim 20, further comprising hydrolysis of the other reaction products to obtain ingenol.

22. The continuous process according to claim 21, further comprising recycling ingenol obtained from the hydrolysis reaction of the other reaction products in the continuous process for forming ingenol-3-mebutate.

* * * * *